United States Patent
Abib

(10) Patent No.: US 7,957,915 B2
(45) Date of Patent: Jun. 7, 2011

(54) PROCESS OF STATISTIC VALIDATION OF CORNEAL ENDOTHELIAL CELLS ANALYSED SAMPLES

(76) Inventor: Fernando Cesar Abib, Curitiba (BR)

( * ) Notice: Subject to any disclaimer, the term of this patent is extended or adjusted under 35 U.S.C. 154(b) by 874 days.

(21) Appl. No.: 11/911,502

(22) PCT Filed: Jul. 29, 2005

(86) PCT No.: PCT/BR2005/000144
§ 371 (c)(1),
(2), (4) Date: Oct. 12, 2007

(87) PCT Pub. No.: WO2006/108250
PCT Pub. Date: Oct. 19, 2006

(65) Prior Publication Data
US 2008/0189050 A1  Aug. 7, 2008

(30) Foreign Application Priority Data
Apr. 15, 2005 (BR) ...................................... 0501384

(51) Int. Cl.
*G01N 33/48* (2006.01)
(52) U.S. Cl. ........................................... 702/21; 725/40
(58) Field of Classification Search ........................ None
See application file for complete search history.

(56) References Cited

U.S. PATENT DOCUMENTS

| 5,523,213 A | 6/1996 | Takahashi et al. |
| 2002/0080329 A1* | 6/2002 | Kasahara ...................... 351/200 |

OTHER PUBLICATIONS

Ruggerie et al. (Br. J. Ophthalmol 89: 306-311, 2005).*

* cited by examiner

*Primary Examiner* — Karlheinz R Skowronek

(57) ABSTRACT

Process of statistic validation of corneal endothelial cells analysed samples", refers to a process complementary to the conventional process known as cornea specular microscopy, by incorporating information obtained by currently available apparatuses, inferring their statistical, and eventually medical, validity, in order to obtain more accurate diagnosis, and better clinical and/or surgical conducts, in so increasing the quality of this procedure to a new level of medical reliability, with the advantages of avoiding that inadequate exams could be considered as valid ones, contribute to diagnosis accuracy, check validity or infirmity of exams already accomplished, guide the eyes bank in the selection and classification of reliability of donated cornea, make use of equipment currently available in the world to improve their own results, identify exams made with not significant sampling, and demonstrate, in a graphic and in numeric form (statistical-analytical rulers).

11 Claims, 3 Drawing Sheets

PROCESS OF STATISTIC VALIDATION OF CORNEAL ENDOTHELIAL CELLS ANALYSED SAMPLES

RELATED APPLICATIONS

This application is a 35 U.S.C. §371 National Stage of PCT/BR2005/000144 filed Jul. 29, 2005 (published as WO2006/108250 on Oct. 19, 2006), which claims priority to BR P1501384-4, filed Apr. 15, 2005.

SUMMARY

Described herein is a process complementary to the conventional process known corneal specular microscopy, which analyzes, according to the patient age, quantity and morphology of the cells in the corneal inner tissue (endothelium), the anatomical structure responsible for maintaining cornea vitality. The process works by incorporating information obtained by currently available apparatuses, inferring their statistical, and eventually medical, validity, in order to obtain more accurate diagnosis, and better clinical and/or surgical conducts, in so increasing the quality of this procedure to a new level of medical reliability, with the advantages of avoiding that inadequate exams could be considered as valid ones, contribute to diagnosis accuracy, check validity or infirmity of exams already accomplished, guide the eyes bank in the selection and classification of reliability of donated cornea, make use of equipment currently available in the world to improve their own results, identify exams made with not significant sampling, demonstrate, in a graphic and in numeric form, the values of variables measured in the examined eye, when compared to average expected values in the patient's age range, demonstrate to the doctor the cases of corneas offering risk in clinical or surgical procedures, additionally demonstrating the relative error regarding the kind of selected and calculated sample, demonstrate, for a same surgeon, endothelial cell loss inherent to the different techniques and kinds of intraocular surgeries (surgeon factor), identify the cases of corneal risk assisting in the planning of medical conduct before a disease, improving the quality of the clinical conduct, the quality of adaptation to contact lenses and assisting in the choice of the better technique and surgical materials, supply data and to enable the use of less sophisticated and older devices with more accuracy in the accomplishment of corneal specular microscopy exams, revitalizing their utilization and avoiding their obsolescence, minimize sampling errors and make easier the understanding of the accomplished exams, allow the doctors who receive the specular microscopy exam in their desks to perform analysis of the obtained sampling validity before valorizing the results of endothelial cells and morphology, allow the doctors to validate or invalidate exams already accomplished by their patients and allow future comparison with past exams considered to be valid.

BRIEF DESCRIPTION OF THE DRAWINGS

For a better understanding of this invention, the following figures are provided.

DETAILED DESCRIPTION

Figure 1:
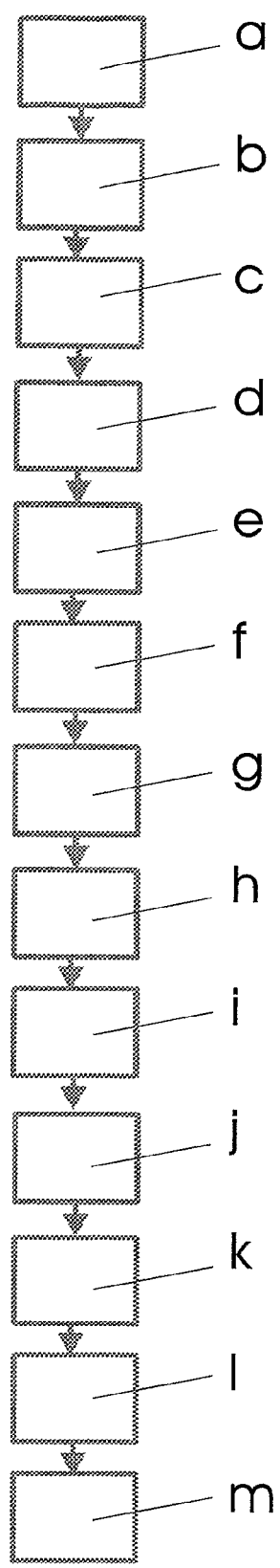
FIG. 1, shows a block diagram of the sequence of the process described herein.

As is known by technicians in the branches of ophthalmology specular microscope industry, a corneal specular microscopy exam has as a goal to analyze the quantity and the morphology of the cells of the corneal internal layer, the endothelium, an anatomical structure responsible for maintaining the cornea vitality (transparency and refractive power).

These cells do not multiply during lifetime; there is a gradual cell death during lifetime. It is necessary to have a minimum quantity of these cells to keep a cornea biologically useful, in other words, transparent and with adequate degree. When these cell populations reach a critical level a cornea loses definitively its transparency, cornea transplant is the only way to restoring vision to the patient.

Nowadays there are several devices that examine the corneal endothelium cells, through an image obtained via cornea specular microscopy performed by equipment known as a specular microscope.

This kind of equipment is used in the ophthalmology, but it is also necessary in the eye banking routine, trying to measure the vitality of the donated cornea, through an appropriated version of specular microscope, as this routine exam improves the success index in cornea transplants.

The current process for analysis of corneal endothelial cells has the following limitations and evident difficulties:

1. Lack of sampling calculation: none of the currently available devices inform how many cells should be evaluated so that the obtained cell sample would be representative of the total population of these cells in the cornea. Consequence of this limitation: the exam can be considered valid for defining a medical conduct without having a statistical or scientific backing, what could lead to medical acts with false grounding.

2. The consequence of this lack of sampling calculation is the appearance of a great quantity of exams with sampling error.

3. In the statistical universe of already performed, specular microscopy exams coexist, without identification, exams with and without sampling error;

4. The current technology does not detect, in already performed exams, the ones with correct sampling.

5. The current technology does not detect, in already performed exams, the ones with incorrect sampling.

6. The evaluated data need to be compared with data of an average population with the same age range, which does not currently occur. As a consequence: found data have distinct connotation for different ages so that in older individuals a given result can be considered as expected, while for a younger individual this same given result will be indicative of disease, a fact that is not take in account by the current technology.

7. Reference values are not found in the available devices for the detection of changed, decreased values, not even values indicating risk for the ocular health or risk for procedures that have as goal the treatment of ocular diseases.

8. In case of assuming validity for an exam whose results were obtained without the due methodological rigueur, the consequences of medical acts could bring damages to the patient's ocular tissue and vision.

9. In case of evaluating the vitality of a cornea donated for transplant by sampling of endothelial cells examined by corneal specular microscopy, there are the same limitations explained above.

10. The choice of the better receiver for a donated cornea lacks endothelial cell morphometric ground and lacks computer science help that could classify in an objective way the data available for such purpose.

11. In the way of making more and more simple and automated the process of imaging the cornea endothelium by corneal specular microscopy, technical resources have been lost, which would have allowed a representative sampling analysis.

There are several kinds of Corneal Specular Microscopes available in the market, which can be classified according to the existence or not of contact with the cornea being examined.

Contact Corneal Specular Microscope: In this device, it is necessary to have physical contact between cornea and the objective lens.

Non-contact Corneal Specular Microscope: In this device, no contact is needed between cornea being analyzed and the optic part of the device objective lens.

According to the data analysis form, corneal specular microscopes are classified as follows:

1. Non-automated Corneal Specular Microscope: the equipment does not offer resources for endothelial evaluation, hence the operator remains responsible for this evaluation, by means of comparison of the endothelium being analyzed with pre-determined grids that supply endothelial density and cellular morphology standards: pleomorphism and polymegatism.

2. Semi-automated Corneal Specular Microscope: This device offers resources for endothelial analysis, however it is necessary that interaction occurs between the operator, the software and the captured endothelial image in order to supply the estimate value of the endothelial density and cellular morphology: pleomorphism and polymegatism.

3. Automated Corneal Specular Microscope: This device offers resources for the endothelial analysis, without a need to interact with the device software or with the captured endothelial image in order to supply the estimate of the endothelial density and cellular morphology: pleomorphism and polymegatism.

Currently, the Corneal Specular Microscopy Exam is performed as follows:

The cells of the corneal endothelium do not multiply and are disposed in a single, thin layer with a thickness of approximately 5 μm. The endothelium is evaluated from a sample obtained by a corneal specular microscope, this sample is taken in the form of an image digitized from video-capture with a mean microscopic increase of 500 times, which represents approximately 1/16 of an area of 1 mm.

A corneal specular microscopy exam evaluates endothelial density, mean cellular size, variation coefficient, percentage of cells with less than six sides, with six sides and with more than six sides, and shape factor.

These evaluated data can be commented as follows:

1. Cellular Density:

This parameter has the goal of demonstrating, through sample(s) of endothelial cells captured by the equipment, the quantity of cells existent in each $mm^2$ of endothelial surface the posterior face of cornea. It is noteworthy that, when the cell population falls to a critical low level, cornea lacks definitively its transparency, corneal transplantation being the only way of restituting its biological functions.

2. Endothelial Cells Morphology 2.1. Mean Cellular Size or Mean Cellular Area

These measured cells are disposed in a single layer and have a flattened form; they are studied in their posterior surface by what is called mean cellular area or size.

2.2 Pleomorphism

Morphology of normal endothelial cell is mainly hexagonal in shape, a little part of these cells population can be a different number of sides, being less than six sides or more than six sides.

This form of variation of the number of sides is called pleomorphism, and is indicative of a lowering of the functional reserve of these cells, or even of stress or suffering. This aspect of cellular morphology is evaluated by the percentage of cells with less than six sides, with six sides, and with more than six sides.

2.3 Polymegatism

The endothelial cell population presents normally a determined standard deviation of size around an average size. This dispersion is called polymegatism and is also an indicative of decrease in the functional reserve of these cells or even stress or suffering. This aspect of these cells morphology is evaluated by the variation coefficient.

2.4 Shape Factor

Another way of studying these cells morphology is through the shape factor, which indicates the regularity of the hexagonal shape in these cells.

All of these data which evaluate the cornea endothelium are influenced by age, in other words, present a variation during lifetime.

Besides these factors, there are specific cornea diseases that can compromise the quantity and vitality of these cells, as well as the use of contact lenses or even the intraocular surgery can cause alterations in this tissue.

It is important to note that the knowledge of the quantity and characteristics of these cells helps the doctor in the conduction of the patient's case, in the choice of the better conduct, decreases risks, and also is used in eyes banks to define the vitality of corneas donated for transplants.

The following factors influence the Endothelium of the Cornea:

3.1 Age

All of these above mentioned data, which evaluate the cornea endothelium, are influenced by age, in other words, they present variation during lifetime and become more pronounced with passing of years.

3.2 Ocular Diseases

Besides these factors, there are specific cornea diseases that can compromise the quantity and vitality of these cells.

3.3 Contact Lenses

The use of contact lenses can cause important alterations in the endothelial cell morphology, so that the specular microscopy exam is a parameter for a biological monitoring of contact lenses users cornea.

3.4 Intraocular Surgery

All intraocular surgical procedure infers to the corneal endothelium a certain loss of its cellularity.

3.5 Cornea Donation

The donated cornea loses vitality until the moment of the transplant.

3.6 Cornea Transplant

Cornea transplant determines, importantly, endothelial cellular loss as to whether a transplant recipient may need a new transplant.

It is noteworthy that the knowledge of the quantity and characteristics of these cells helps the doctor in the conduction of the patient's case, in the choice of better conduct, diminished risks, and also, for these motivations, such knowledge is used in eyes banks to define the vitality of corneas donated for transplants.

Among the devices available in the market, whether out of production and in use, or currently in production and in use, the following specular microscopes are some examples:

BIO-OPTICS LSM 12000, LSM 12000 CT, LSM 2200, LSM 2100E, LSM 2100C, LSM 2000C, Konan NONCON ROBO SP-6000, NONCON ROBO PACHY SP-9000, CELL CHECK, SEED SP-500, TOPCON SP 1000 and SP-2000P, TOMEY IN-1100, Keeler Konan, ProEB4, Hexgrid, Procem 4, Cell Max contact-type and non-contact type, confocal microscopes NIDEK CONFOSCAN 3 and CORNEA CONFOCAL HRT II.

What all of these listed devices do is to calculate the median and/or mean and standard deviation for cellular density, average cellular size, variation coefficient, percentage of cells with less than six, six and more than six sides, and shape factor.

Some devices evaluate a few of these parameters, other are more complete and evaluate all of them, however, none of them supplies a comparison of the values found in the patient in exam with the average values found in the normal population to the same age. Besides that, they do not supply any indication of the quantity of cells to be evaluated so that the examined sample has statistical validity and consequently clinical validity.

All the above listed equipment obtains a cell sample that can be statistically analyzed. This sample can be considered valid or not valid, taking in account the confidence level and relative error that an accurate statistical analysis could supply. None of the listed equipment accomplishes this analysis to validate or not the samples obtained by them, because when developed this preoccupation was not considered.

A process of statistical validation of analyzed corneal endothelial cell samples was developed to overcome the limitations, disadvantages and problems of conventional processes. Such a statistical validation process can be complementary with current technology, not making it obsolete, but on the contrary, allowing for incorporating the information obtained by currently available equipment, inferring from such information statistical and consequently clinical validity for better defining diagnosis and clinical and/or surgical conducts, by incorporating information obtained by currently available apparatuses, inferring their statistical, and eventually medical, validity, in order to obtain more accurate diagnosis, and better clinical and/or surgical conducts, in so increasing the quality of this procedure to a new level of medical reliability, with the following characteristics:

1. The process is fed with data supplied from the results of exams accomplished with any of the corneal specular or confocal microscopes in use.

2. A routine of the process makes found results statistically valid and reproducible, what enables a comparative analysis of exams performed in different times, in addition to better define diagnostic and medical-ophthalmologic conducts, whether clinical and/or surgical.

3. The process guides the examiner to obtain an elevated degree of reliability for the cells sample in exam (e.g., "reliability degree"). By degree of reliability it can be understood that among a great number of performed diagnoses there is the least possible number of not diagnosed or false-negative cases, in fact patients that did not have their diagnosis performed, being unnoticed.

4. The process demonstrates by sampling whether the found relative error is small or tolerable, or great or not tolerable.

By relative error can be understood that among a great number of normal cases there is the least possible number of diagnosed or false-positive cases when really they are not, in other words, disease is diagnosed for normal patients.

5. The process also supplies the possibility that the operator determine in the software, levels of elevated confidence level in order to make viable, the sizes of endothelial sample to be obtained in the case in study. For the determined confidence level the process will calculate the respective relative error in the exam being performed, this error guides the doctor in the process of whether to validate or not the result of the specular microscopy. The confidence level demonstrates the probability expressed in percentage, in which the confidence interval contains a value mean found for the variable in study. The confidence interval introduces two limits, a superior and an inferior, both relative to the mean. The inferior limit is defined by the value of the mean minus the percentage of the relative error and the superior limit is the value of the mean plus the percentage of the relative error (Confidence interval=Mean+/−relative error). Thus the exam performed according to the process will make easier future comparisons.

6. Besides these achievements, the process demonstrates in comparative form, if the values found (mean and respective reliability interval) are in conformity with average values expected for patient's age or if they will be considered to be low. In these cases, depending on their magnitude, the values can be indicative of risk for certain medical-ophthalmologic conducts. They also are evidenced graphically.

7. An already performed, past exam can be also submitted to the process analysis to verify, according to a confidence level chosen by the software operator, the relative error of the past exam. Thus, it is possible to sort the statistically valid and the statistically invalid past exams, allowing for viable comparisons with present exams.

8. The calculation of the sample size to be obtained under orientation of the process can be accomplished by two ways:

8.1 By the first way, it is taken in account patient data and epidemiologic corneal data to define the total sample, this method is denominated of Standard Sample.

8.2 By the second way, it is taken in account a patient's endothelial data to provide for feedback in the process so that, based in these values, will be defined the ideal sampling for the eye under analysis, this method is denominated of Personalized Sample (e.g., a customized sample) and is the most objective and accurate way to accomplish the cornea endothelium sampling calculation for the best use of all devices for corneal specular microscopy devices available in the world market.

9. In addition, the process shows to the eye banking technician and to the doctor whether the cornea in routine exam has measures similar to average values expected according to a donor's age or is considered inadequate for transplant, besides assisting in disease detection.

The process described herein has the following advantages:

1. It avoids that inadequately performed exams could eventually and erroneously be considered valid.

2. It contributes to the diagnosis accuracy, improving the conduct and minimizing clinical, medical, and surgical errors.

3. It confers validity or invalidates already performed (past) exams.

4. It guides the eye banking routine in classification of donated cornea viability.

5. It better selects corneas available for transplant.

6. It allows the improvement of results in equipment currently in use worldwide by means of the complementary utilization of the process.

7. It determines the number of cells that should be included in the images acquired by specular or confocal microscopes to compose a standard or personalized sample (e.g., customized sample).

8. It statistically validates the sample in the exam accomplished in patient or donated corneas.

9. It offers reproducibility for the results of these exams.

10. It identifies the exams that were performed without having significant sampling.

11. It shows, in graphic and numeric form, the values of the variables measured in the eye being examined, in comparison with normal people average values in the patient age range.

12. It shows to the doctor the cases of corneas offering risk in clinical or surgical procedures, be it by the decrease of the endothelial density, be it by the variation in the cellular morphology, be it by the association of both factors.

13. In addition, it shows the relative error or cut off regarding the type of selected sample.

14. Results obtained for all variables studied by the process allow comparison, in a serial way, with further exams led by the process.

15. From exams already performed by any brand and model of corneal specular or confocal microscope, at any past time, without any sampling orientation, when analyzed by the process, existing sampling error can be obtained:

15.1 In case of data being valid, these can be compared with exams performed under the process orientation.

15.2 In case of data being non-valid, these cannot be compared with exams performed under the process orientation.

15.3 In case of data being invalid, however with a relative error very close to the planned, the doctor decides if this low difference between planned and calculated error could be disregarded, having in mind the fact that this exam was performed in the past.

16. It shows, for a same surgeon, the endothelial cells loss inherent to the different techniques and kinds of intraocular surgeries (surgeon factor).

17. It identifies the cases of risks to the cornea, assisting in the planning of the medical conduct before a disease, improving the quality of the clinical conduct, of the contact lenses adaptation and assisting in the choice of the better technique and surgical materials.

18. It allows the device users, even in the simplest and older equipments, to attain solid results in the performance of corneal specular microscopy exams, revitalizing equipment utilization. For that, it is sufficient to supply the endothelial density and the number of cell counting in order to make calculations for the Standard Sample and, in case of equipment that also supply the variation coefficient, the Personalized Sample (e.g., customized sample) can be obtained.

19. The process does not cause obsolescence of equipment currently used, on the contrary, it improves their results.

20. The process minimizes sampling errors and facilitates the understanding of the performed exams.

21. The process allows the doctors who receive the corneal specular microscopy exam in their desks to accomplish analysis of the sampling validity, obtained before taking values of results of endothelial cellularity and morphology.

22. The process allows the doctors to validate or invalidate exams that their patients already have accomplished.

Figure 2:
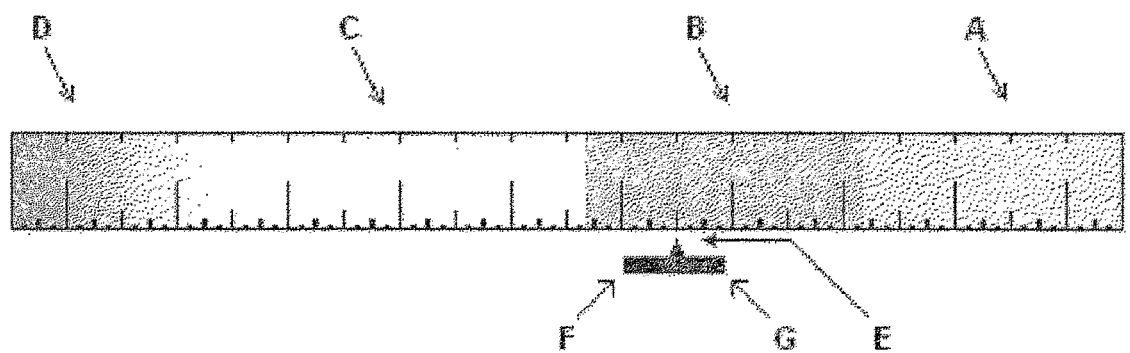
FIG. 2, shows the statistical-analytical ruler type graph for a graphic visualization of endothelial data results studied and obtained by the process. In this case, the presented ruler is an example of the result of endothelial density.
Figure 3:
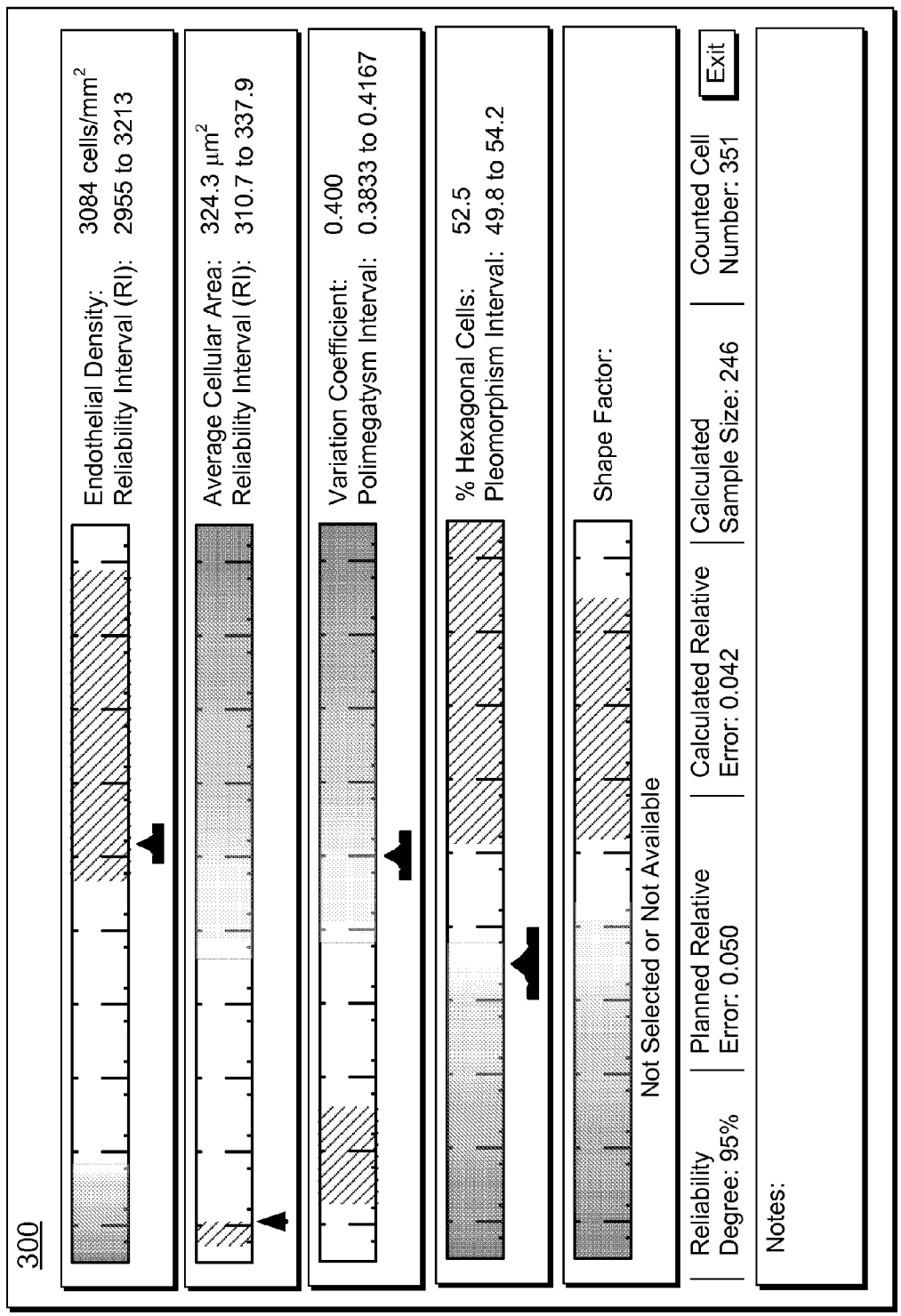
FIG. 3, shows a report graphic that includes multiple statistical-analytical and reliability degree (e.g., degree of reliability), planned relative error, calculated relative error, calculated sample size, and counted cell number.

The process for statistical validation of cornea samples and analysis of cornea endothelial cells here presented is realized by dedicated software specially developed for accomplishment of the process from the statistical data obtained in corneal specular microscopy devices currently available in the market, taking in account patient age, having integrating among referred devices and the process, being the software operatively coupled or not operatively coupled to the referred devices, and the process accomplished in the following sequence, for example, as shown in FIG. 1:

a. Initially, data of the clinic, examiner doctor, requesting doctor, and corneal specular microscope used in image acquisition are configured;

b. Patient data are identified: name, date of birth and age;

c. Routine to be accomplished is requested: to guide an exam being realized or to validate an already realized, past exam needed to inform past exam date;

d. Data supplied by the specular microscopy exam are entered: endothelial density, average cellular area, number of counted cells, variation coefficient, cells with less than six, with six, and with more than six sides, and shape factor (they can be one or more than one);

e. The sampling type is selected: Standard for corneal specular microscopes that do not calculate the variation coefficient, or personalized (e.g., customized) in case the variation coefficient is known. When the specular microscope supplies the variation coefficient the user can choose between the Standard or Personalized sampling type;

f. Statistical power of the sample to be calculated is determined: 90% to 99% confidence level and 10% to 1% for planned relative error;

g. Sample size and calculated relative error or cut off are determined;

h. Graphic and numeric demonstrations of the sample size are shown:

Graphic and numeric demonstration of the quantity of counted cells and of the number of cells that composes the Standard Sample;

Graphic and numeric demonstration of the quantity of counted cells and of the number of cells that composes the Personalized Sample;

Graphic and numeric demonstration of the quantity of counted cells and, of the number of cells that composes the Standard Sample and of the number of cells that composes the Personalized Sample (simultaneously);

i. Numeric visualization of the calculated relative error determined for the number of cells that composes the chosen sample;

j. Graphic visualization of the values found for the studied variables: endothelial density, average cellular area, number of counted cells, variation coefficient, cells with less than six, six and more than six sides, and shape factor, presented in statistical-analytical rulers in a rectangular format with stripes (areas) positioned side by side in any direction (from A to D or from D to A), where, for example, as shown in FIG. 2:

A. Area indicating values above that expected for the age (located in the side opposite to degradee color);

B. Area indicating values expected for the age;

C. Area indicating values lower than expected for the age, however within the biological reserve compatible with a normal function;

D. Area indicating values considered critical for the age; the intensity of the color increases as the evaluated data becomes more critical E. Arrow indicating the mean of the studied variable;

F. Indicates the inferior limit of the reliability interval (RI) for the studied variable;

G. Indicates the superior limit of the reliability interval (RI) for the studied variable; and F-G segment: represents the reliability interval (RI) which is calculated as follows: RI=mean+/−relative error calculated for the total sample, assuming variable length, accompanying in the used scale, the value of the calculated reliability intervals the, F-G segment and can be positioned below, within, or above the stripes that define the areas.

k. An area is generated for written considerations about endothelial cells morphometry, endothelial analysis and final conclusions and another clear area is created for optional description of analyzed data (endothelial density, average cellular area, number of counted cells, variation coefficient, cells with less than six, six and more than six sides, and shape factor);

l. An area is generated for input of diagnosis found in the endothelial and morphometric analysis of the cornea, and another clear area is created for the optional description of the conclusion based on results evidenced by the process, where the doctor makes considerations relative to the clinical-surgical historic; and m. The reports are printed:

For exams accomplished under the orientation of the process:

Graphics: statistical-analytical rulers for each one of the studied variables (endothelial density, average cellular area, variation coefficient, percentage of cells with less than six, six and more than six sides and shape factor), individually issued for each eye (see, e.g., the graphic report 300 of FIG. 3);

Sampling: Type of selected sample: standard or personalized (e.g., customized) with respective statistical power (confidence level and relative error), individually issued for each eye;

Descriptive (mean for the studied variables and, if available, standard deviation), where the data for each eye are presented in comparative form);

Final analysis: descriptive report at choice of the doctor responsible for the process, or Complete: compounded by all four reports above described; or To validate already accomplished exams:

Sample analyzed with respective statistical power, individually issued for each eye; or Descriptive (mean of the studied variables), where data for each eye are presented in comparative form.

As an example, consider a process for statistical validation of analyzed corneal endothelial cell samples realized through implementation of software. Such a process can operate on data obtained from one or more corneal specular microscopy devices. Such a process can be characterized by taking into account patient information (e.g., name, date of birth and age), selecting a routine to be accomplished (e.g., to guide an exam being realized or to validate an already realized, past exam), supplying and entering exam data (e.g., endothelial density, average cellular area, number of counted cells, variation coefficient, cells with less than six, with six, and with more than six sides, and shape factor), selecting sampling type (e.g., "Standard" for specular microscopes that do not calculate the variation coefficient, or "Personalized" (e.g., customized) in case the variation coefficient is known, where the specular microscope supplies the variation coefficient the user can choose between the Standard or Personalized sampling type), determining or calculating statistical power of the sample (e.g., 90% to 99% for confidence level and 10% to 1% for relative error), and determining sample size and calculating relative error.

A process can include displaying graphic and numeric demonstrations of the sample size, quantity of counted cells and of the number of cells that composes a sample (e.g., Standard Sample or Personalized Sample), quantity of counted cells and, of the number of cells that compose a Standard Sample and of the number of cells that compose a Personalized Sample (e.g., optionally simultaneously) (see, e.g., the graphic report 300 of FIG. 3).

A process can include display (e.g., visualization) of the calculated relative error determined for the number of cells that composes a chosen sample. A process can include display (e.g., visualization) of values found for studied variables such as endothelial density, average cellular area, number of counted cells, variation coefficient, cells with less than six, six and more than six sides, and shape factor. Such display or visualization can be presented with one or more statistical-analytic rulers, for example, in a rectangular format with stripes (areas) positioned side by side in any direction. For example, for areas from A to D or from D to A where:

A. Area indicating values above that expected for the age (located in the side opposite to degradee color);

B. Area indicating values expected for the age;

C. Area indicating values lower than expected for the age, however within the biological reserve compatible with a normal function; and D. Area indicating values considered critical for the age (e.g., where intensity of color increases as the evaluated data becomes more critical).

Other features can include:

E. Arrow indicating the mean of the studied variable;

F. Indicating the inferior limit of the reliability interval (RI) for the studied variable;

G. Indicating the superior limit of the reliability interval (RI) for the studied variable; and F-G segment. Representing the reliability interval (RI) which is calculated as follows: RI=mean+/−relative error calculated for the total sample, assuming variable length, accompanying in the used scale, the value of the calculated reliability interval, F-G segment and can be positioned below, within, or above the stripes that define the areas.

As described herein, an area can be generated for written considerations about endothelial cells morphometry, endothelial analysis and final conclusions and another clear area can be created for optional description of analyzed data (endothelial density, average cellular area, number of counted cells, variation coefficient, cells with less than six, six and more than six sides, and shape factor).

As described herein, a clear area can be generated for input of diagnosis found in the endothelial and morphometric analysis of the cornea, and another clear area can be created for the optional description of the conclusion based on results evidenced by a process, where the doctor makes considerations relative to the clinical-surgical historic.

As described herein, reports can be printed. For exams accomplished under the orientation of a process, graphics can include: statistical-analytical rulers for each one of the studied variables (endothelial density, average cellular area, variation coefficient, percentage of cells with less than six, six and more than six sides and shape factor), individually issued for each eye; sampling type of selected sample such as standard or personalized with respective statistical power (confidence level and relative error), individually issued for each eye; descriptive information (mean for the studied variables and, if available, standard deviation), where the data for each eye are presented in comparative form); final analysis information as a descriptive report at choice of the doctor responsible for a process; or a complete report, for example, compounded by all four of the aforementioned reports. As to validation of already accomplished exams, a report (e.g., displayed or otherwise visualized) can include sample analyzed with respective statistical power, individually issued for each eye. In a descriptive (e.g., mean of the studied variables) presentation, data for each eye can be presented in comparative form (see, e.g., the graphic report 300 of FIG. 3).

As described herein, a process can include use of data supplied by the results of exam accomplished with any of the corneal specular or corneal confocal microscopes in operation.

As described herein, a process can include turning previously found results statistically valid and reproducible for medical help.

As described herein, a process can include obtaining elevated confidence level for the cell sample under exam, showing whether the found relative error in samples is small or tolerable, great or not tolerable and to determine levels of elevated reliability degrees to make possible that the sample endothelial size be obtained in the case in study.

As described herein, a process can include allowing that an already accomplished, past exam can also be submitted to process analysis to verify, in the confidence level chosen by the doctor, its own relative error or cut off value.

As described herein, a process can include calculation of sample size, in Standard or Personalized form, being obtained under orientation of the process.

As described herein, a process can include showing to the eye banking technician and to the doctor whether the cornea in routine exam has measures similar to that average values expected according to donor's age or is considered inadequate for transplant, besides assisting in the diseases detection.

As described herein, a process can include showing, for a same surgeon, the endothelial cells loss inherent to the different techniques and kinds of intraocular surgeries (surgeon factor).

As described herein, a process can include showing, in graphic and numeric form, the values of the variables measured in the eye being examined, in comparison with normal people average values in the patient age range.

As described herein, a process can include identifying the cases of risks to the cornea, assisting in the planning of the medical conduct.

As described herein, a process can include supplying data and allowing the device users, even in the simplest and older equipments, to attain solid results in the performance of corneal specular microscopy exams, revitalizing equipment utilization.

As described herein, a process can include allowing the doctors who receive the corneal specular microscopy exam in their desks to accomplish analysis of the sampling validity, obtained before taking values of results of endothelial cellularity and morphology.

As described herein, a process can include allowing the doctors to validate or invalidate exams that their patients already have accomplished and the results allowing comparison, in a serial way, with further exams led by the process.

As described herein, a process can include providing a statistical-analytical ruler, for graphic visualization of the values found for the studied variables, in a rectangular format with stripes (areas) positioned side by side in any direction (from A to D or from D to A) and with F-G segment positioned below, within, or above the areas A, B, C and D (see, e.g., the ruler of FIG. 2 and the graphic report 300 of FIG. 3).

The invention claimed is:

1. A process operatively coupled to a microscope device, the device configured to calculate values for variables wherein the variables comprise members selected from a group consisting of median and/or mean and standard deviation for corneal cellular density; average cellular area; variation coefficient; percentage of corneal cells with less than six sides; percentage of corneal cells with six sides; percentage of corneal cells with more than six sides; and shape factor, the process comprising:

generating using the device a statistical-analytic ruler graphic for a variable wherein the ruler graphic comprises areas A, B, C and D wherein area A indicates values of the variable above that expected for age of a corneal cell sample, area B indicates values of the variable expected for age of the corneal cell sample, area C indicates values of the variable lower than expected for age of the corneal cell sample and within a biological reserve compatible with normal corneal function, and area D indicates values of the variable considered critical for age of the corneal cell sample;

generating an arrow graphic E that indicates mean of the variable for the corneal cell sample;

generating a segment graphic F-G wherein an F end of the segment indicates an inferior limit of a reliability interval for the variable, wherein a G end of the segment indicates a superior limit of the reliability interval for the variable, and wherein the segment length from F to G represents a reliability interval calculated according to a mean plus and minus a relative error calculated for the corneal cell sample; and generating a report graphic that comprises at least the ruler graphic for the variable.

2. The process of claim 1 wherein the generating a report graphic generates a report graphic that comprises one or more additional ruler graphics for one or more other variables.

3. The process of claim 1 wherein the generating a report graphic generates a report graphic that comprises information for a reliability degree and information for a comparison between a planned relative error and a calculated relative error.

4. The process of claim 1 wherein the generating a report graphic generates a report graphic that comprises information for a comparison between a calculated corneal sample size and a counted corneal cell number.

5. The process of claim 1 wherein the generating a report graphic generates a report graphic that comprises information for a comparison between a calculated corneal sample size and a counted corneal cell number, information for a reliability degree and information for a comparison between a planned relative error and a calculated relative error.

6. The process of claim 1 wherein the generating a report graphic generates a report graphic that comprises one or more additional ruler graphics for one or more other variables, information for a comparison between a calculated corneal sample size and a counted corneal cell number, information for a reliability degree and information for a comparison between a planned relative error and a calculated relative error.

7. A process comprising:
performing a corneal examination with a microscope;
receiving information from the corneal examination;
providing a planned relative error for the examination;
calculating a relative error for the examination
generating a reliability graphic based on the planned relative error and the relative error; and
presenting the reliability to a display as feedback for improving the degree of reliability during the examination.

8. The process of claim 7 wherein the providing a planned relative error comprises providing a planned relative corneal cell sample size error and wherein the calculating the relative error comprises calculating a relative corneal cell sample size error.

9. The process of claim 8 wherein the received information comprises providing a number of counted cells and wherein the calculating a relative corneal cell sample size error depends on the number of counted cells.

10. The process of claim 9 wherein the presenting the reliability graphic provides for feedback to increase the number of counted cells to improve the degree of reliability of the examination being performed.

11. The process of claim 7 wherein the received information comprises personal information about a subject cornea and further comprising performing a statistical analysis based at least in part on the personal information, generating a ruler graphic based at least in part on the statistical analysis, and presenting the ruler graphic to a display.

* * * * *